United States Patent [19]
Lee

[11] Patent Number: 4,560,752
[45] Date of Patent: Dec. 24, 1985

[54] PHOSPHINATES OR PHOSPHONATES USEFUL FOR CONTROL OF WEEDS

[75] Inventor: Shy-Fuh Lee, Sunnyvale, Calif.

[73] Assignee: Zoecon Corporation, Palo Alto, Calif.

[21] Appl. No.: 625,394

[22] Filed: Jun. 28, 1984

Related U.S. Application Data

[63] Continuation-in-part of Ser. No. 585,742, Mar. 2, 1984, abandoned, which is a continuation-in-part of Ser. No. 518,520, Jul. 29, 1983, abandoned.

[51] Int. Cl.$^4$ ............................................. C07D 273/00
[52] U.S. Cl. ........................................ 544/66; 71/71; 71/86; 71/87; 260/941; 260/942; 260/943; 260/944; 260/948; 260/950; 260/954; 260/956; 260/502.4 R; 544/182; 544/183; 544/232; 544/237; 546/23; 546/24

[58] Field of Search ................. 544/66, 182, 183, 232, 544/237; 546/23, 24; 260/502.4 N, 941, 942, 943, 944, 948, 950, 954, 956; 71/71, 86, 87

[56] References Cited
U.S. PATENT DOCUMENTS 4,478,832  10/1984  King .................................. 260/944

Primary Examiner—Maurice J. Welsh
Attorney, Agent, or Firm—Hana Dolezalova; Jacqueline S. Larson

[57] ABSTRACT

Novel 5-(substituted amino)phenoxyalkyl-, phenylthioalkyl-, phenylsulfinylalkyl-, and phenylsulfonylalkyl-phosphinates and phosphonates, synthesis thereof, intermediates therefor, and the use of said novel compounds for the control of weeds.

27 Claims, No Drawings

PHOSPHINATES OR PHOSPHONATES USEFUL FOR CONTROL OF WEEDS

This is a continuation-in-part of Ser. No. 585,742, filed Mar. 2, 1984, now abandoned, which is a continuation-in-part of Ser. No. 518,520, filed July 29, 1983 now abandoned.

The present invention relates to novel 5-(substituted amino)phenoxyalkyl-, phenylthioalkyl-, phenylsulfinylalkyl-, and phenylsulfonylalkylphosphinates and phosphonates, synthesis thereof, intermediates therefor, and the use of said novel compounds for the control of weeds.

More particularly, the novel compounds of the present invention are represented by the following formula (A):

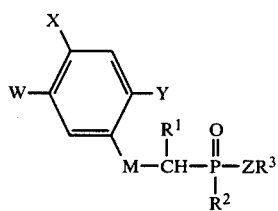

wherein,

M is oxygen, sulfur, sulfinyl or sulfonyl;
W is selected from the groups

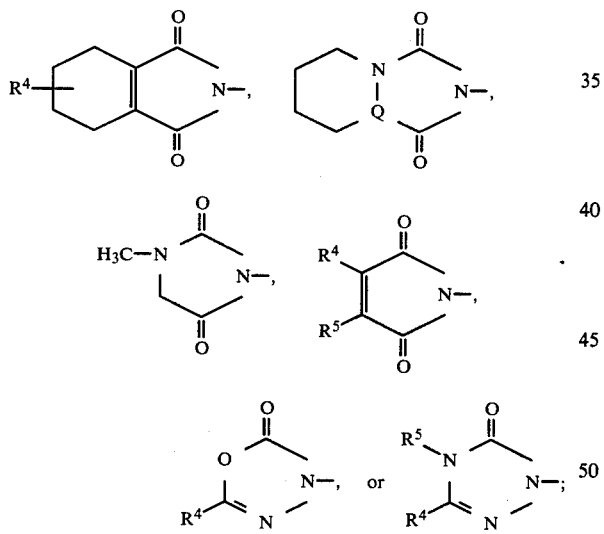

Q is N or CH;
each of X and Y is independently hydrogen or halogen;
Z is O, S or NR';
each of R' and $R^1$ is independently hydrogen or lower alkyl;
$R^2$ is lower alkyl or lower alkoxy;
$R^3$ is hydrogen, lower alkyl, lower alkenyl, lower alkynyl, cycloalkyl, alkoxyalkyl, alkylthioalkyl, alkoxycarbonylalkyl or dialkylaminocarbonylalkyl; and
each of $R^4$ and $R^5$ is independently hydrogen or lower alkyl.

In the description and claims hereinafter, each of $R^1$-$R^5$, R', M, Q, W, X, Y and Z is as defined above, unless otherwise specified.

The compounds of the present invention of formula B can be synthesized by the reaction of an amino compound of formula (IV) with 3,4,5,6-tetrahydrophthalic anhydride, in the presence of an acid such as acetic acid.

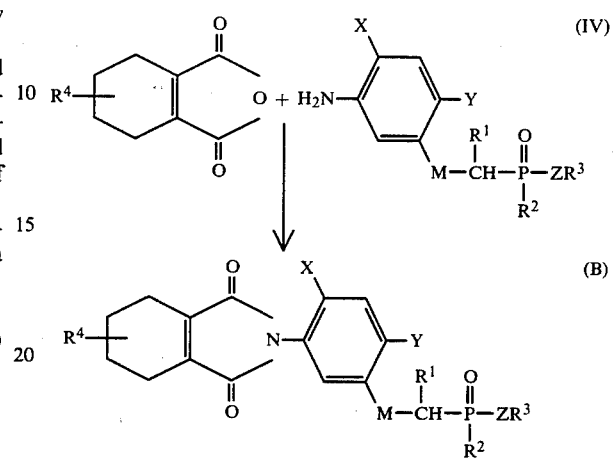

The compounds of the present invention of formula C can be prepared by reacting 2-alkoxycarbonylhexahydropyridine (formula IX) with phosgene in a base such as triethylamine and a solvent such as benzene to give N-chlorocarbonyl-2-alkoxycarbonylhexahydropyridine (formula X). A compound of formula X is then reacted with an amino compound of formula IV at a temperature above room temperature such as the reflux temperature to give a tetramethylenehydantoin of formula C. ($R^8$ is lower alkyl.)

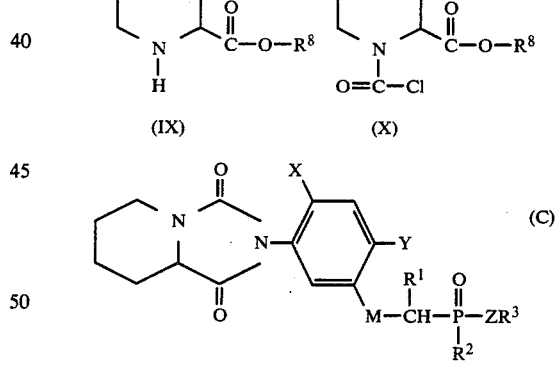

The compounds of formula D can be prepared as above by reaction of N-alkoxycarbonylhexahydropyridazine (formula XI) with phosgene to give N-chlorocarbonyl-N'-alkoxycarbonylhexahydropyridazine (formula XII), which is then reacted with a compound of formula IV.

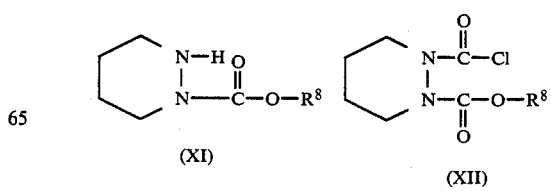

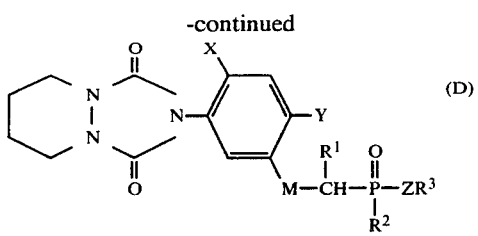

Alternatively, a compound of formula IV can be treated with trichloromethylchloroformate and dioxane to give an isocyanate of formula (XIII), which is then reacted with either 2-alkoxycarbonylhexahydropyridine hydrochloride or N-alkoxycarbonylhexahydropyridazine hydrochloride in a base such as triethylamine and a solvent such as benzene or methylene chloride to prepare the compounds of formula C or formula D, respectively.

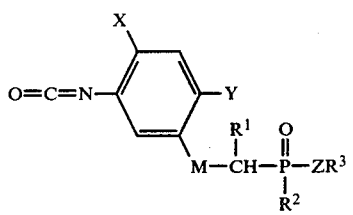

The compounds of formula E can be prepared as above by the reaction of a compound of formula XIII with methyl N-methylaminoacetate hydrochloride, followed by reaction with a strong acid such as HCl.

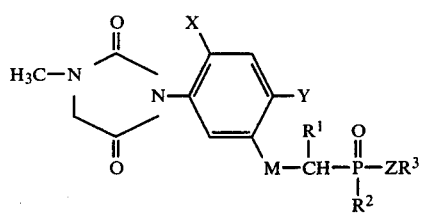

The compounds of formula F can be prepared by the reaction of an amino compound of formula IV with a substituted maleic anhydride in the presence of acetic acid.

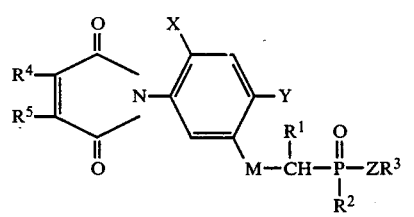

To prepare the compounds of formula G, an amino compound of formula IV is reacted with sodium nitrite and then with stannous chloride in HCl at a temperature below RT to give a hydrazine of formula XVII. The hydrazine is reacted with an acid chloride of the formula

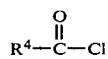

in the presence of a base such as triethylamine and a solvent such as methylene chloride and at RT or below to give the hydrazine of formula XVIII, which is then treated with phosgene in dioxane or with trichloromethylchloroformate and triethylamine in dioxane to give a compound of formula G.

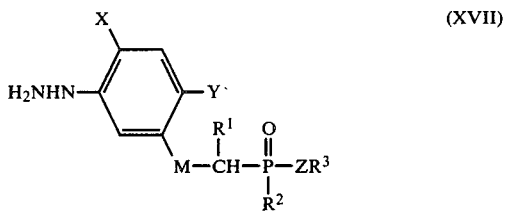

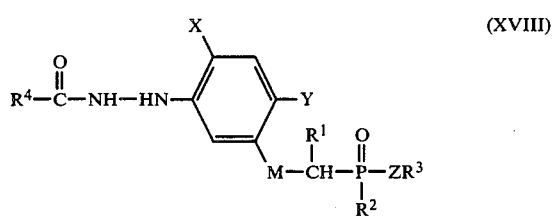

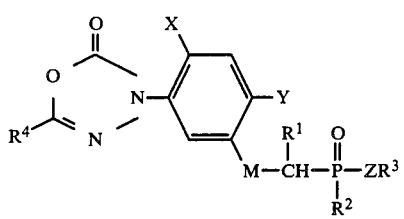

The compounds of formula H can be prepared by reaction of a hydrazine of formula XVII with an acylurea of the formula

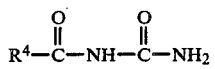

at elevated temperature and in the presence of a solvent such as decahydronaphthalene to give compounds of formula H where $R^5$ is hydrogen. Such compounds can be reacted with a halide $R^5$-XX (XX=halide) to prepare compounds of formula H where $R^5$ is lower alkyl.

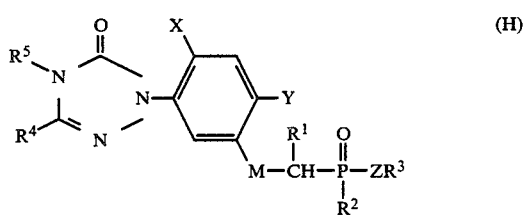

The compounds of formula IV where M is oxygen, Z is oxygen, $R^3$ is lower alkyl and X is other than fluoro can be synthesized as outlined below:

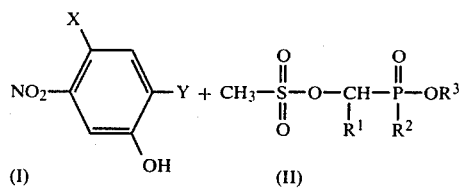

(I)     (II)

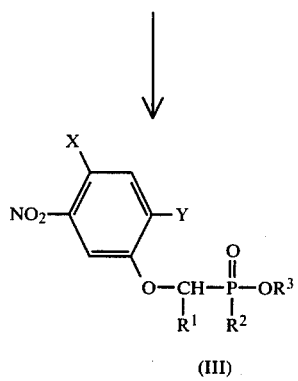

(III)

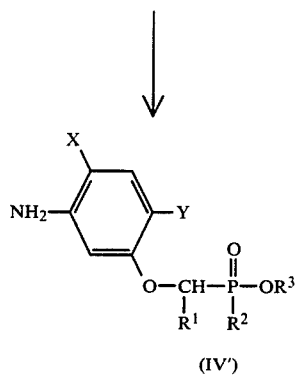

(IV')

In the above synthesis, a nitrophenol (I) is reacted with a sulfonate (II) (where $R^2$=lower alkyl) to give a nitrophenoxyalkylphosphinate (III), which is then hydrogenated to the corresponding amino compound (IV').

The compounds of formula (IV') where $R^2$ is lower alkoxy are prepared by the reaction of a nitrophenol of formula (I) with an alcohol of formula (XIV) (where $R^2$=lower alkoxy) to give a nitrophenoxyalkylphosphonate (III), which is then hydrogenated, following the procedure of S. Bittner and Y. Assaf, *Chem. Ind. (London)* (6):281 (1975).

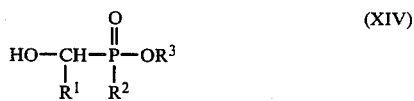

(XIV)

To prepare compounds of formula IV' where the values of X include fluoro, an aminophenol of formula (XV) is reacted with either a sulfonate of formula (II) or an alcohol of formula (XIV) to give directly the corresponding aminophenoxy compound (IV').

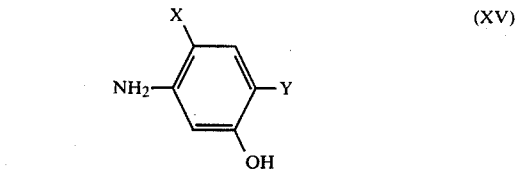

(XV)

To prepare compounds of formula IV where $R^3$ is other than lower alkyl or where Z is sulfur or amino, a compound of formula III or of formula IV' (where $R^3$ is lower alkyl) is halogenated by reaction with, for example, thionyl chloride or oxalyl chloride, and the resulting halophosphinate or phosphonate (VI; R is $NO_2$ or $NH_2$ and XX is halo) is reacted with a compound of the formula $R^3$—ZH. Where R is $NO_2$, the resulting compound is then hydrogenated to the corresponding amino compound (IV).

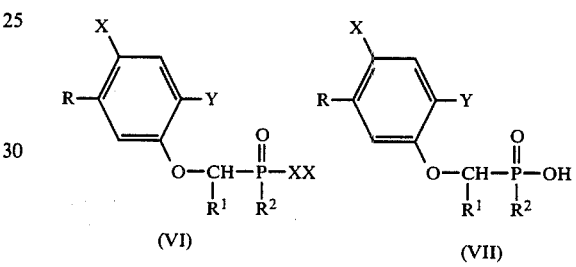

(VI)     (VII)

In an alternative method for preparing compounds of formula (IV) where $R^3$ is alkoxycarbonylalkyl, a compound of formula (VI) is hydrolyzed to the corresponding phosphinic or phosphonic acid (VII). A compound of formula (VII) is then reacted with a halide of formula (VIII) to give a compound of formula (XVI) ($R^6$ is hydrogen or lower alkyl, and $R^7$ is lower alkyl). Where R is $NO_2$, the resulting compound is then hydrogenated.

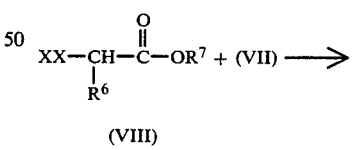

(VIII)

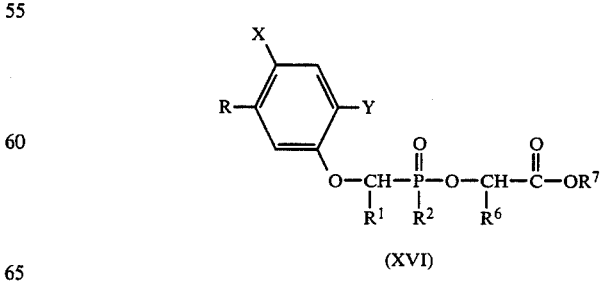

(XVI)

The compounds of formula IV where M is sulfur can be prepared as outlined below:

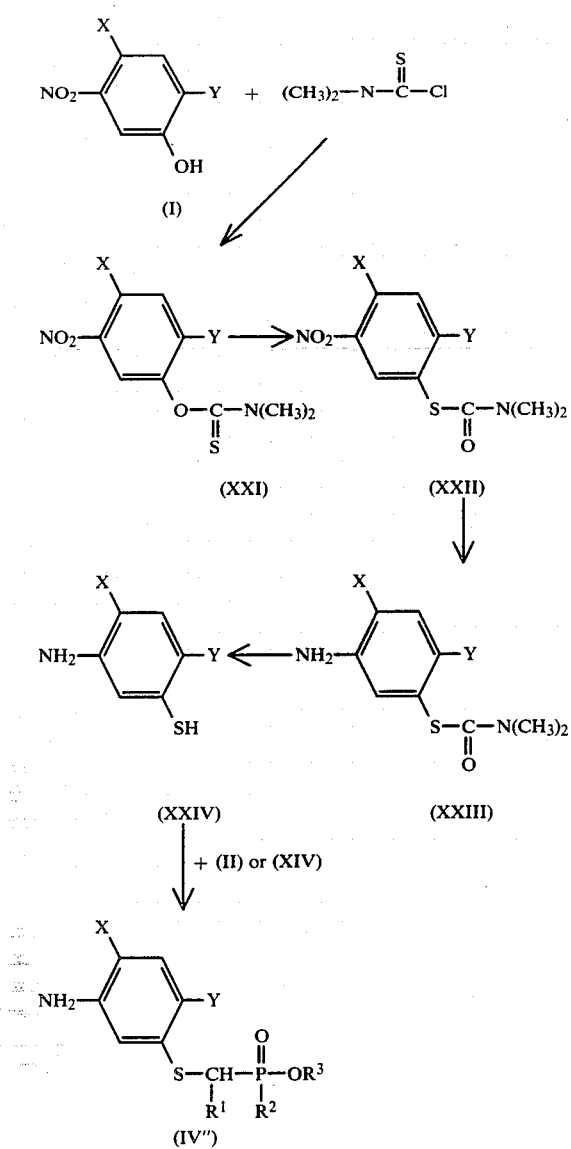

In the above synthesis, a nitrophenol (I) is reacted with dimethylthiocarbamoyl chloride in the presence of 1,4-diazabicyclo(2,2,2-octane) (Dabco) to give an O-nitrophenyldimethylthiocarbamate (XXI), which is then converted to the S-nitrophenylthiocarbamate (XXII) by heating at an elevated temperature, ~230°, following the procedure described by Newman & Karness, *J. Org. Chem.* 31:3980 (1966). The compound XXII is hydrogenated to the corresponding S-aminophenylthiocarbamate (XXIII), which is reacted with aqueous sodium hydroxide in a solvent such as methanol or ethanol and at elevated temperature to give an aminophenylthiol (XXIV). The thiols XXIV are then reacted with a sulfonate (II) or an alcohol (XIV) following the procedures described hereinabove to give a compound of formula (IV").

To prepare compounds of formula A where M is sulfinyl, a compound of formula A where M is sulfur is reacted with one equivalent of m-chloroperbenzoic acid in a solvent such as methylene chloride. To prepare compounds of formula A where M is sulfonyl, two equivalents of m-chloroperbenzoic acid are reacted with a compound A where M is sulfur.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms.

The term "lower alkoxy" refers to an alkoxy group, straight or branched, having a chain length of one to eight carbon atoms.

The term "lower alkenyl" refers to an alkenyl group, straight or branched, having a chain length of two to eight carbon atoms and one or two ethylenic bonds.

The term "lower alkynyl" refers to an alkynyl group, straight or branched, having a chain length of two to eight carbon atoms and one or two acetylenic bonds.

The term "cycloalkyl" refers to a cycloalkyl group of three to eight carbon atoms.

The term "alkoxyalkyl" refers to an alkoxyalkyl group of two to eight carbon atoms.

The term "alkoxycarbonylalkyl" refers to an alkoxycarbonylalkyl group of three to nine carbon atoms.

The term "alkylthioalkyl" refers to an alkylthioalkyl group of two to eight carbon atoms.

The term "dialkylaminocarbonylalkyl" refers to a dialkylaminocarbonylalkyl group of four to nine carbon atoms.

The compounds of the present invention have one or more asymmetric carbon atoms. The present invention includes each of the optically active isomers and racemic mixtures thereof. In the examples hereinafter, unless otherwise specified, the compound prepared is a racemic mixture.

The novel compounds of formula (A) are useful for the control of weeds, using pre- and/or post-emergent treatments. The compounds can be applied in the form of dusts, granules, solutions, emulsions, wettable powders, flowables and suspensions. Application of a compound of the present invention is made according to conventional procedure to the weeds or their locus using an herbicidally effective amount of the compounds, usually from about one-half or less to ten pounds per acre.

Methods of preparing herbicidal formulations which can be used with a compound of the present invention are described in the literature along with suitable liquid and solid carriers, such as in U.S. Pat. No. 4,192,669 and 4,163,661, which are incorporated herein by reference. The optimum usage of a compound of the present invention is readily determinable by one of ordinary skill in the art using routine testing such as greenhouse testing and small plot testing.

The term "herbicide," as used herein, refers to an active ingredient which modifies the growth of plants because of phytotoxic or plant growth regulating properties so as to retard the growth of the plant or damage the plant sufficiently to kill it.

While the compounds of the present invention have activity on grass weeds, the compounds, in general, demonstrate a higher level of herbicidal activity on broadleaf plants. Broadleaf plant (weed) species on which the compounds of the present invention show effective herbicidal activity include, but are not limited to, mustard, pigweed, velvetleaf, jimsonweed, cocklebur, sicklepod and annual morning glory. Many of the compounds of formula A exhibit excellent tolerance for corn.

The compounds of the present invention, in view of their broadspectrum broadleaf weed herbicidal activity, can be advantageously combined with grass weeds herbicides for broadspectrum postemergence weed control in most grass crops. Examples of herbicides which can be combined with a compound of the present invention include those selected from the carbamates, thiocarbamates, chloroacetamides, dinitroanilines, benzoic acids, glycerol ethers, pyridazinones, uracils and ureas for controlling a broad spectrum of weeds.

The following examples are provided to illustrate the practice of the present invention. Temperature is given in degrees Centigrade. "RT" means room temperature.

EXAMPLE 1

To a solution of 2,4-dichloro-5-nitrophenol (630 mg, 3.0 mmo.) dissolved in 7 ml of dimethylsulfoxide (DMSO) is added potassium carbonate (538 mg, 3.9 mmol) and ethyl P-methyl($\alpha$-methylsulfonyloxyethyl)phosphinate (966 mg, 4.2 mmol). The mixture is stirred at 75° under $N_2$ overnight. The reaction is diluted and acidified with 10% HCl and extracted (3X) with methylene chloride. The combined extracts are washed with water (3X), dried over sodium sulfate and evaporated to dryness. The resulting crude product is purified by column chromatography to give ethyl P-methyl-[$\alpha$-(2,4-dichloro-5-nitrophenoxy)ethyl]phosphinate.

Iron metal powder (1.5 g) is added in small portions to a stirring solution of ethyl P-methyl-[$\alpha$-(2,4-dichloro-5-nitrophenoxy)ethyl]phosphinate (1000 mg, 2.9 mmol) in 5% aqueous acetic acid, and the mixture is heated at 115°-120° for 35 minutes. The reaction mixture is allowed to cool to RT and is made alkaline with potassium carbonate, filtered and extracted with methylene chloride. The combined extracts are washed with water (3X), dried over sodium sulfate and evaporated to dryness to give ethyl P-methyl[$\alpha$-(2,4-dichloro-5-aminophenoxy)ethyl]phosphinate.

The above aminophenoxyethylphosphinate (500 mg, 1.6 mmol) is dissolved in glacial acetic acid. 3,4,5,6-Tetrahydrophthalic anhydride (292 mg, 1.9 mmol) is added to the solution. The mixture is heated at 100° under $N_2$ overnight and then at 140° for an additional 6 hours. It is allowed to cool to RT, adjusted to pH 5-6 with potassium carbonate, diluted with water and extracted with methylene chloride. The extracts are combined, dried over sodium sulfate and evaporated to dryness to give, following purification by prep. thin layer chromatography (TLC), N-{5-[$\alpha$-(ethyl P-methylphosphino)ethoxy]-2,4-dichlorophenyl}tetrahydrophthalimide, MS m/e 446.3 (M+) (compound 1, Table A).

EXAMPLE 2

Following the procedure of Example 1, 2,4-dichloro-5-nitrophenol (3.0 g, 14.4 mmol) and ethyl P-methyl ($\alpha$-methylsulfonyloxy-n-propyl)phosphinate (4.6 g, 18.7 mmol) are reacted together to give ethyl P-methyl-[$\alpha$-(2,4-dichloro-5-nitrophenoxy)-n-propyl]phosphinate. This phosphinate is then hydrogenated to the corresponding amino compound, which is then reacted with 3,4,5,6-tetrahydrophthalic anhydride to give the final product N-{5-[$\alpha$-(ethyl P-methylphosphino)n-propoxy]-2,4-dichlorophenyl}tetrahydrophthalimide (compound 2, Table A).

EXAMPLE 3

Thionyl chloride (8 ml) is added to ethyl P-methyl-[$\alpha$-(2,4-dichloro-5-nitrophenoxy)-n-propyl]phosphinate, prepared as in Example 2 above, and the mixture is allowed to stand at RT overnight. The thionyl chloride is removed and the resulting P-methyl-[$\alpha$-(2,4-dichloro-5-nitrophenoxy)-n-propyl]phosphinic acid chloride is treated with 2.0 g of sodium hydroxide in water (100 ml). The aqueous solution is acidified and extracted with ether, and the ether extracts are dried and evaporated to dryness to give P-methyl-[$\alpha$-(2,4-dichloro-5-nitrophenoxy)-n-propyl]phosphinic acid.

The above phosphinic acid (1.7 g) is dissolved in 10 ml of ether, and an excess of diazomethane is added. After reaction is complete, excess diazomethane is decomposed with acetic acid and the solution is concentrated to dryness to give methyl P-methyl-[$\alpha$-(2,4-dichloro-5-nitrophenoxy)-n-propyl]phosphinate.

Following the procedures of Example 1, the above phosphinate is hydrogenated to the corresponding amino compound (1.1 g, 3.5 mmol), which is then reacted with 3,4,5,6-tetrahydrophthalic anhydride (0.69 g, 4.6 mmol) to yield N-{5-[$\alpha$-(methyl P-methylphosphino)n-propoxy]-2,4-dichlorophenyl}tetrahydrophthalimide, MS m/e 446.27 (M+) (compound 3, Table A).

EXAMPLE 4

Following the procedure of Example 1, each of 2-chloro-5-nitrophenol, 2,4-difluoro-5-nitrophenol, 2-chloro-4-fluoro-5-nitrophenol and 2-bromo-4-chloro-5-nitrophenol is reacted with methyl P-methyl($\alpha$-methylsulfonyloxy-n-propyl)phosphinate, followed by hydrogenation and reaction with 3,4,5,6-tetrahydrophthalic anhydride to yield, respectively, compounds numbered 4, 5, 6, and 7 in Table A.

In the same way, 2-chloro-4-fluoro-5-nitrophenol and ethyl P-methyl($\alpha$-methylsulfonyloxy-n-propyl)phosphinate are combined, hydrogenated and reacted with tetrahydrophthalic anhydride to give compound 20 in Table A.

EXAMPLE 5

Following the procedure of Example 1, each of the phosphinates under column I is reacted with 2,4-dichloro-5-nitrophenol, followed by hydrogenation and reaction with 3,4,5,6-tetrahydrophthalic anhydride to give the corresponding tetrahydrophthalimide in Table A.

I 8. methyl P-methyl(methylsulfonyloxymethyl)phosphinate.
9. methyl P-ethyl($\alpha$-methylsulfonyloxyethyl)phosphinate.
10. methyl P-n-propyl($\alpha$-methylsulfonyloxyethyl)phosphinate.
11. methyl P-methyl($\alpha$-methylsulfonyloxyisobutyl)phosphinate.
12. methyl P-methyl($\alpha$-methylsulfonyloxy-n-butyl)phosphinate.
21. methyl P-ethyl($\alpha$-methylsulfonyloxy-n-propyl)phosphinate.
37. methyl P-methyl($\alpha$-methylsulfonyloxyethyl)phosphinate.

EXAMPLE 6

Following the procedure of Example 3, methyl[α-(2,4-dichloro-5-nitrophenoxy)ethyl]phosphinic acid is prepared from ethyl P-methyl[α-(2,4-dichloro-5-nitrophenoxy)ethyl]phosphinate.

A mixture of the above phosphinic acid (1.5 g, 5.59 mmol), potassium carbonate (0.9 g), methyl bromoacetate (1.2 g, 0.74 ml, 7.80 mmol) and acetone (20 ml) is heated under reflux overnight. The reaction mixture is allowed to cool to RT and filtered, and the filtrate is concentrated. The only residue is extracted in methylene chloride and the extracts are washed, dried and evaporated to dryness to give methoxycarbonylmethyl P-methyl[α-(2,4-dichloro-5-nitrophenoxy)ethyl]phosphinate.

The above phosphinate is suspended in 5% acetic acid (50 ml) and iron powder (2.0 g) is added. The mixture is heated under reflux for one hour. After cooling to RT, the reaction mixture is filtered, and the filtrate is extracted with methylene chloride. The combined extracts are dried over magnesium sulfate and concentrated to dryness to give, after purification by prep. TLC, methoxycarbonylmethyl P-methyl[α-(2,4-dichloro-5-aminophenoxy)ethyl]phosphinate.

The above aminophenoxy phosphinate (1.2 g, 4.10 mmol), 3,4,4,6-tetrahydrophthalic anhydride (0.75 g, 4.90 mmol) and acetic acid (4 ml) are mixed together and heated under reflux for about 6 hours. The solution is concentrated to dryness and any excess starting anhydride is removed in vacuo. The crude product is purified by prep. TLC to give N-{5-[α-(methoxycarbonylmethyl P-methylphosphino)ethoxy]-2,4-dichlorophenyl}tetrahydrophthalimide (compound 13, Table A).

Following the above procedures, each of ethyl[α-(2,4-dichloro-5-nitrophenoxy)ethyl]phosphinic acid, methyl[α-(2,4-dichloro-5-nitrophenoxy)-n-propyl]phosphinic acid, methyl(2,4-dichloro-5-nitrophenoxy)methylphosphinic acid and methyl[α-(2-chloro-4-fluoro-5-nitrophenoxy)-n-propyl]phosphinic acid is prepared and reacted with methyl bromoacetate, followed by hydrogenation and reaction with 3,4,5,6-tetrahydrophthalic anhydride to yield, respectively, compounds 14, 15, 22 and 49 in Table A.

EXAMPLE 7

Methyl[α-(2,4-dichloro-5-nitrophenoxy)-n-propyl]phosphinic acid chloride (1.0 g, from Example 3, 2-propenol (1.3 g), triethylamine (1.2 g) and methylene chloride (10 ml) are combined and allowed to sit at RT for 2 hours, followed by aqueous work-up, to give 2-propenyl P-methyl[α-(2,4-dichloro-5-nitrophenoxy)-n-propyl]phosphinate. In the same way, each of methoxyethanol, cyclopropanol and methylthiomethanol is reacted with methyl[α-(2,4-dichloro-5-nitrophenoxy)-n-propyl]phosphinic acid chloride to give the corresponding phosphinate.

Folowing the procedure of Example 1, each of the above four phosphinates is hydrogenated and reacted with 3,4,5,6-tetrahydrophthalic anhydride to give, respectively, compounds numbered 16, 17, 18 and 19 in Table A.

TABLE A

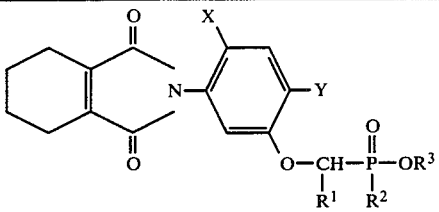

| Cpd | X | Y | R¹ | R² | R³ | MS (m/e) |
|---|---|---|---|---|---|---|
| 1 | Cl | Cl | CH₃ | CH₃ | CH₂CH₃ | 446.3 |
| 2 | Cl | Cl | CH₂CH₃ | CH₃ | CH₂CH₃ | |
| 3 | Cl | Cl | CH₂CH₃ | CH₃ | CH₃ | 446.27 |
| 4 | H | Cl | CH₂CH₃ | CH₃ | CH₃ | 411.0 |
| 5 | F | F | CH₂CH₃ | CH₃ | CH₃ | |
| 6 | F | Cl | CH₂CH₃ | CH₃ | CH₃ | |
| 7 | Cl | Br | CH₂CH₃ | CH₃ | CH₃ | |
| 8 | Cl | Cl | H | CH₃ | CH₃ | 418.22 |
| 9 | Cl | Cl | CH₃ | CH₂CH₃ | CH₃ | 446.29 |
| 10 | Cl | Cl | CH₃ | CH₂CH₂CH₃ | CH₃ | 460.30 |
| 11 | Cl | Cl | CH(CH₃)₂ | CH₃ | CH₃ | |
| 12 | Cl | Cl | CH₂CH₂CH₃ | CH₃ | CH₃ | |
| 13 | Cl | Cl | CH₃ | CH₃ | CH₂C(O)OCH₃ | 490.28 |
| 14 | Cl | Cl | CH₃ | CH₂CH₃ | CH₂C(O)OCH₃ | 504.31 |
| 15 | Cl | Cl | CH₂CH₃ | CH₃ | CH₂C(O)OCH₃ | 504.31 |
| 16 | Cl | Cl | CH₂CH₃ | CH₃ | CH₂CH=CH₂ | |
| 17 | Cl | Cl | CH₂CH₃ | CH₃ | CH₂CH₂OCH₃ | |
| 18 | Cl | Cl | CH₃CH₃ | CH₃ | CH—CH₂ \ / CH₂ | |
| 19 | Cl | Cl | CH₃CH₃ | CH₃ | CH₂SCH₃ | |
| 20 | F | Cl | CH₂CH₃ | CH₃ | CH₂CH₃ | |
| 21 | Cl | Cl | CH₂CH₃ | CH₂CH₃ | CH₃ | 460.00 |
| 22 | Cl | Cl | H | CH₃ | CH₂C(O)OCH₃ | 476.25 |
| 23 | F | Cl | H | CH₂CH₃ | CH₂CH₃ | 429.0 |
| 24 | F | Cl | H | CH₂CH₃ | CH(CH₃)₂ | 443 |
| 25 | F | Cl | CH₃ | CH₂CH₂CH₃ | CH₂CH₃ | 457 |
| 26 | F | Cl | CH₃ | CH₂CH₃ | CH₂CH₃ | 443 |
| 27 | F | Cl | CH₃ | CH₃ | CH₂CH₃ | 429 |
| 28 | F | Cl | CH₂CH₃ | CH₂CH₃ | CH₂CH₃ | 457 |
| 29 | F | Cl | H | CH₂CH₃ | CH₂CH(CH₃)₂ | 457 |
| 30 | F | Cl | H | CH₂CH₃ | CH₂CH₂OCH₃ | 459 |
| 31 | F | Cl | CH₂CH₃ | CH₃ | CH₂CH=CH₂ | 455 |
| 32 | F | Cl | CH₃ | CH₂CH₂CH₃ | CH₂CH₂OCH₃ | 487 |
| 33 | F | Cl | CH₂CH₃ | CH₃ | CH₂CH₂OCH₃ | 473 |
| 34 | F | Cl | CH₂CH₃ | CH₃ | CH₂C≡CH | 453.6 |
| 35 | H | Cl | CH₂CH₃ | CH₂CH₃ | CH₃ | 425.8 |
| 36 | H | Cl | CH₂CH₃ | CH₂CH₃ | CH₂CH₃ | 439.9 |
| 37 | Cl | Cl | CH₃ | CH₃ | CH₃ | 432.2 |
| 38 | F | Cl | H | CH₃ | CH₂CH₃ | 415.8 |
| 39 | F | Cl | CH₃ | CH(CH₃)₂ | CH₂CH₃ | 457.8 |
| 40 | F | Cl | CH₂CH₂CH₃ | CH₃ | CH₂CH₃ | 457.8 |
| 41 | F | Cl | H | CH₂CH₂CH₃ | CH₃ | 429.8 |
| 42 | F | Cl | H | CH₂CH₃ | CH₃ | 415.8 |
| 43 | H | Cl | CH₂CH₃ | CH₃ | CH₂CH₃ | 425.8 |
| 44 | H | Cl | H | CH₂CH₃ | CH₂CH₃ | 411.8 |
| 45 | H | Cl | CH₃ | CH₂CH₂CH₃ | CH₂CH₃ | 439.9 |
| 46 | H | Cl | CH₃ | CH₂CH₃ | CH₂CH₃ | 425.8 |
| 47 | H | Cl | CH₃ | CH₂CH₃ | CH₃ | 411.8 |
| 48 | H | Cl | H | CH₂CH₃ | CH₃ | 397.8 |
| 49 | F | Cl | CH₂CH₃ | CH₃ | CH₂C(O)OCH₃ | 487.8 |

EXAMPLE 8

Pre-emergent herbicidal activity of compounds 1 and 3 of the present invention was determined as follows: Seeds of selected weeds were planted and the soil was drenched with a solution of water (17%), surfactant (0.17%) and the test compound at a rate equivalent to 10 lb/acre and 3.3 lb/acre. Scoring was made two weeks after treatment. In the 10 lb/acre test, the grasses (GR) green foxtail, watergrass, shattercane and wild oats and the broadleafs (BL) annual morning glory, mustard, nightshade and velvetleaf were treated. In the 3.3 lb/acre test, the grasses green foxtail, barnyard grass, bermuda grass, wild oats and downy brome and the broadleafs mustard, pigweed, velvetleaf, jimsonweed, cocklebur, sicklepod and annual morning glory were tested. The average pre-emergent activity of the two compounds is presented in Table B below.

EXAMPLE 9

Post-emergence herbicidal activity of compounds 1 and 3 was tested as follows: Seedlings of selected weeds were sprayed with a solution of water/acetone (1:1), surfactant (0.5%) and the test compound at a rate equivalent to 10 lb/acre and 3.3 lb/acre. Scoring was made two weeks after spraying. In the 10 lb/acre test, the grasses (GR) green foxtail, water grass, shattercane and wild oats and the broadleafs (BL) annual morning glory, mustard, soybean and velvetleaf were treated. In the 3.3 lb/acre test, the grasses green foxtail, barnyard grass, bermuda grass and wild oats and the broadleafs annual morning glory, pigweed, velvetleaf, cocklebur and sicklepod were treated. The average post-emergent activity of compounds 1 and 3 are presented in Table B below.

EXAMPLE 10

A mixture of 2-chloro-4-fluoro-5-aminophenol (0.60 g, 3.72 mmol) in 10 ml of DMSO, potassium carbonate (0.62 g, 4.40 mmol) and ethyl P-ethyl(methylsulfonyloxymethyl)phosphinate (1.19 g, 5.21 mmol) is heated to 100° for 48 hours. The reaction mixture is diluted with ether and filtered, and the filtrate is washed with brine, dried and evaporated to dryness. The crude product is purified by prep. TLC to give ethyl P-ethyl(2-chloro-4-fluoro-5-aminophenoxy)methylphosphinate.

A mixture of the above phosphinate (0.77 g, 2.61 mmol) and 3,4,5,6-tetrahydrophthalic anhydride (0.52 g, 3.39 mmol) in 5 ml of acetic acid is heated under reflux for 9 hours. Excess anhydride and acetic acid are removed in vacuo. The oily product is purified by prep. TLC to give N-[5-(ethyl P-ethylphosphinomethoxy)-4-chloro-2-fluorophenyl]tetrahydrophthalimide, MS m/e 429 (M+) (compound 23, Table A).

nmr (CDCl$_3$) $\tau$ 8.87, 8.65 (tt, 3H, P—CH$_2$—CH$_3$), 8.70 (t, 3H, O—CH$_2$—CH$_3$), 5.93 (q, O—CH$_2$—CH$_3$), 5.82 (d, 2H, P—O—CH$_2$—CH$_3$), [3.15 (d, 1H), 2.77 (d, 1H)-aromatic H].

EXAMPLE 11

Following the procedure of Example 10, each of the phosphinates under column II is reacted with 2-chloro-4-fluoro-5-aminophenol, followed by reaction with 3,4,5,6-tetrahydrophthalic anhydride to give the corresponding tetrahydrophthalimide in Table A.

II 24. isopropyl P-ethyl(methylsulfonyloxymethyl)phosphinate.
25. ethyl P-n-propyl (α-methylsulphonyloxyethyl)phosphinate.
26. ethyl P-ethyl(α-methylsulfonyloxyethyl)phosphinate.
27. ethyl P-methyl(α-methylsulfonyloxyethyl)phosphinate.
28. ethyl P-ethyl(α-methylsulfonyloxy-n-propyl)phosphinate.
38. ethyl P-methyl(methylsulfonyloxymethyl)phosphinate.
39. ethyl P-isopropyl(α-methylsulfonyloxyethyl)phosphinate.
40. ethyl P-methyl(α-methylsulfonyloxybutyl)phosphinate.
41. methyl P-n-propyl(methylsulfonyloxymethyl)phosphinate.
42. methyl P-ethyl(methylsulfonyloxymethyl)phosphinate.

EXAMPLE 12

A solution of ethyl P-ethyl(2-chloro-4-fluoro-5-aminophenoxy)methylphosphinate (1.50 g, 5.10 mmol) in thionyl chloride (6 ml) is heated under reflux with stirring and under N$_2$ for 1.5 hours. The excess thionyl chloride is removed in vacuo and methylene chloride (12 ml) is added, followed by dropwise addition of isobutyl alcohol (6 ml). After addition is complete, the mixture is stirred at RT under N$_2$ for 18 hours. The reaction mixture is diluted with methylene chloride, washed with potassium carbonate and sodium chloride and evaporated to dryness. The crude product is purified by prep. TLC to give isobutyl P-ethyl-(2-chloro-4-fluoro-5-aminophenoxy)methylphosphinate. Following the procedure of Example 10, the above isobutyl phosphinate (0.94 g, 2.9 mmol) is reacted with 3,4,5,6-tetrahydrophthalic anhydride (0.57 g, 3.8 mmol) to give N-[5-(isobutyl P-ethylphosphinomethoxy)-4-chloro-2-fluorophenyl]tetrahydrophthalimide, MS m/e 457 (M+) (compound 29, Table A).

nmr (CDCl$_3$ $\tau$ 9.04 (d, 6H, CH(CH$_3$)$_2$), 8.92, 8.54 (tt, 3H, P—CH$_2$—CH$_3$), 8.20 (m, 8H, CH$_2$—CH$_2$, P—CH$_2$—CH$_3$, O—CH$_2$—CH(CH$_3$)$_2$), 5.77 (d, 2H, OCH$_2$—P), [3.15 (d, 1H), 2.80 (d, 1H)-aromatic H].

EXAMPLE 13

Following the procedure of Example 12, ethyl P-ethyl-(2-chloro-4-fluoro-5-aminophenoxy)methylphosphinate is reacted with thionyl chloride and then with 2-methoxyethanol (6 ml) to give 2-methoxyethyl P-ethyl-(2-chloro-4-fluoro-5-aminophenoxy)methylphosphinate (1.07 g, 3.3 mmol), which is then reacted with 3,4,5,6-tetrahydrophthalic anhydride (0.65 g, 4.3 mmol) to yield N-[5-(2-methoxyethyl P-ethylphosphinomethoxy)-4-chloro-2-fluorophenyl]tetrahydrophthalimide, MS m/e 459 (M+) (compound 30, Table A).

nmr (CDCl$_3$) $\tau$ 8.92, 8.52 (tt, 3H, P—CH$_2$—CH$_3$), 8.16 (m, 6H, CH$_2$—CH$_2$, P—CH$_2$—CH$_3$), 6.70 (s, 3H, O—CH$_3$), 6.47 (t, 2H, O—CH$_2$—CH$_2$—O—CH$_3$), 5.87 (t, 2H, O—CH$_2$—CH$_2$—O—CH$_3$), 5.70 (d, 2H, O—CH$_2$—P), [3.10 (d, 1H), 2.77 (d, 1H)-aromatic H].

In the same way, ethyl P-methyl-1-(2-chloro-4-fluoro-5-aminophenoxy)propylphosphinate (1.00 g, 3.2 mmol) is reacted with thionyl chloride (4 ml) and then with allyl alcohol (4 ml) to give allyl P-methyl-1-(2-chloro-4-fluoro-5-aminophenoxy)propylphosphinate. The allyl phosphinate (0.59 g, 1.8 mmol) is then reacted with 3,4,5,6-tetrahydrophthalic anhydride (0.36 g, 2.4 mmol) to give N-{5-[α-(allyl P-methylphosphino)-n-propoxy]-4-chloro-2-fluorophenyl}tetrahydrophthalimide, MS m/e 455 (M+) (compound 31, Table A).

In the same manner as above, ethyl P-methyl-1-(2-chloro-4-fluoro-5-aminophenoxy)propylphosphinate is reacted with thionyl chloride and then with propargyl alcohol to give propargyl P-methyl-1-(2-chloro-4-fluoro-5-aminophenoxy)propylphosphinate, which is then reacted with 3,4,5,6-tetrahydrophthalic anhydride to give N-{5-[α-(propargyl P-methylphospino)-n- propoxy]-4-chloro-2-fluorophenyl}tetrahydrophthalimide, MS m/e 453.6 (M+) (compound 34, Table A).

Following the same procedures, each of ethyl P-n-propyl-1-(2-chloro-4-fluoro-5-aminophenoxy)ethylphosphinate and ethyl P-methyl-1-(2-chloro-4-fluoro-5-aminophenoxy)propylphosphinate is reacted with thionyl chloride and then with 2-methoxyethanol to give, respectively, 2-methoxyethyl P-n-propyl-1-(2-chloro-4-fluoro-5-aminophenoxy)ethylphosphinate and 2-methoxyethyl P-methyl-1-(2-chloro-4-fluoro-5-aminophenoxy)propylphosphinate, each of which is then reacted with 3,4,5,6-tetrahydrophthalic anhydride to yield the final products:

N-{5-[α-(2-methoxyethyl P-n-propylphosphino)ethoxy]-4-chloro-2-fluorophenyl}tetrahydrophthalimide, MS m/e 487 (M+) (compound 32, Table A); and N-{5-[α-(2-methoxyethyl P-methylphosphino)-n-propoxy]-4-chloro-2-fluorophenyl}tetrahydrophthalimide, MS m/e 473 (M+) (compound 33, Table A).

EXAMPLE 14

A mixture of ethyl P-methyl-1-(2-chloro-4-fluoro-5-aminophenoxy)propylphosphinate (1.00 g, 3.2 mmol) and trichloromethylchloroformate (0.76 g, 0.46 ml, 3.9 mmol) in dioxane (50 ml) and triethylamine (0.36 g, 0.49 ml, 3.5 mmol) is heated for 3 hours. The dioxane is then removed in vacuo to give the corresponding isocyanate, which residue is taken up in methylene chloride (35 ml). Ethyl pipecolinate [2-(ethoxycarbonyl)hexahydropyridine] (0.754 g, 0.75 ml, 4.8 mmol) is added and the mixture is stirred at RT overnight. The reaction mixture is diluted with methylene chloride, washed with water, dried and evaporated to dryness. The resulting urea compound (1.5 g, 3.2 mmol) is dissolved in ethanol (15 ml). 2N HCl (20 ml) is added, and the solution is heated under reflux for 5 hours and then at 90° overnight. The ethanol is removed in vacuo, and the residue is diluted with water, extracted with methylene chloride (3X). The combined extracts are dried and evaporated to dryness. The crude product is purified by prep. TLC to give 3-{5-[α-(ethyl P-methylphosphino)-n-propoxy]-4-chloro-2-fluorophenyl}-1,5-tetramethylenehydantoin, MS m/e 446 (M+) (compound 50, below).

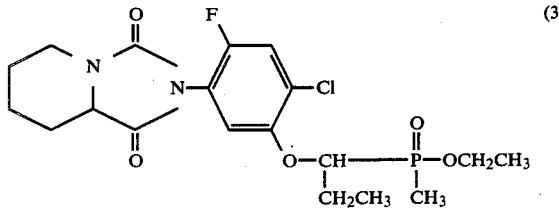

(34)

EXAMPLE 15

A mixture of ethyl P-methyl-1-(2,4-dichloro-5-aminophenoxy)propylphosphinate (2.20 g, 6.7 mmol) and trichloromethylchloroformate (1.60 g, 0.97 ml, 8.1 mmol) in dioxane (50 ml) and triethylamine (0.81 g, 1.1 ml, 8.1 mmol) is heated for 3.5 hours. The dioxane is removed in vacuo and the resulting isocyanate is taken up in methylene chloride (60 ml). Triethylamine (1.02 g, 1.4 ml, 10.1 mmol) and methyl methylaminoacetate hydrochloride (1.40 g, 10.1 mmol) are added, and the mixture is stirred at RT for 1 hour. The reaction mixture is diluted with methylene chloride, washed with water, dried and evaporated to dryness. To the resulting urea compound (2.5 g), dissolved in ethanol (15 ml), is added 2N HCl (20 ml) and the mixture is stirred at RT for ~60 hours. The mixture is then heated under reflux for 7 hours, followed by stirring at RT overnight. The ethanol is then removed in vacuo, and the residue is diluted with water and extracted with methylene chloride. The combined extracts are dried and purified by prep. TLC to give 1-methyl-3-{5-[α(ethyl P-methylphosphino)-n-propoxy]-2,4-dichlorophenyl}hydantoin, MS m/e 423 (M+) (compound 51; XIX, X=Cl).

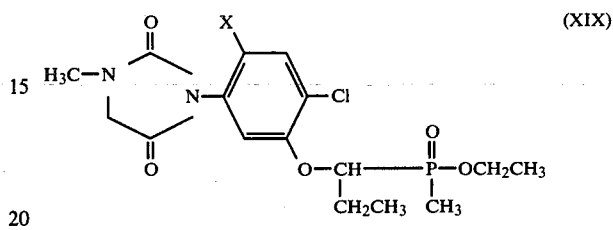

(XIX)

In the same manner, ethyl P-methyl-1-(2-chloro-4-fluoro-5-aminophenoxy)propylphosphinate (1.00 g, 3.2 mmol) and trichloromethylchloroformate (0.76 g, 0.46 ml, 3.9 mmol) are reacted together, and the resulting isocyanate is reacted with methyl methylaminoacetate hydrochloride (0.67 g, 4.8 mmol). The resulting urea compound (3.2 mmol) is heated together with 2N HCl (8 ml) and purified to give 1-methyl-3-{5-[α-(ethyl P-methylphosphino)-n-propoxy]-4-chloro-2-fluorophenyl}hydantoin, MS m/e 406 (M+) (compound 52; XIX, X=F).

EXAMPLE 16

Following the procedure of Example 14, ethyl P-methyl-1-(2-chloro-4-fluoro-5-aminophenoxy)propylphosphinate is treated with trichloromethylchloroformate, and the resulting isocyanate is reacted with N-ethoxycarbonylhexahydropyridazine hydrochloride, followed by heating to give 4-{5-[α-(ethyl P-methylphosphino)-n-propoxy]-4-chloro-2-fluorophenyl}-1,2-tetramethylenetriazolidine-3,5-dione (compound 53, below).

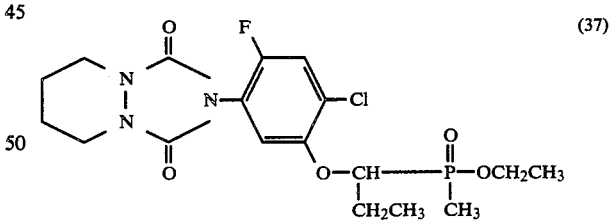

(37)

EXAMPLE 17

Methyl P-ethyl-(2-chloro-4-fluoro-5-aminophenoxy)-methylphosphinate (3.4 mmol) is dissolved in 6N HCl (10 ml). Temperature of the solution is maintained at −15° to −20° as sodium nitrite (0.24 g, 3.5 mmol) in 2 ml of water is added dropwise. The mixture is warmed to 0° and is stirred at 0° for 1 hour. An ice-cooled solution of stannous chloride/2H2O in 2 ml of conc. HCl is quickly added to the mixture, and stirring at 0° is continued for 2.5 hours. The reaction mixture is neutralized with saturated sodium bicarbonate and is extracted with methylene chloride. The combined extracts are washed with water, dried, evaporated to dryness and purified by prep. TLC to give methyl P-ethyl-(2-chloro-4-fluoro-5-hydrazinophenoxy)methylphosphinate.

To the above phosphinate (2.5 mmol) in methylene chloride (10 ml) is added pivaloyl chloride (3.0 mmol) and triethylamine (3.0 mmol). The mixture is stirred at RT for 4 hours, after which it is washed with water, dried and evaporated to dryness to give methyl P-ethyl-[2-chloro-4-fluoro-5-(N'-pivaloylhydrazino)phenoxy]methylphosphinate.

A mixture of the above pivaloylhydrazino compound (3.2 mmol), trichloromethylchloroformate (3.9 mmol) and triethylamine (3.5 mmol) in dioxane (50 ml) is heated for 3.5 hours. The dioxane is then removed in vacuo. The product is diluted with methylene chloride, washed, dried, evaporated to dryness and purified by prep. TLC to give 2-t-butyl-4-[5-(methyl P-ethylphosphinomethoxy)-4-chloro-2-fluorophenyl]-$\Delta^2$-1,3,4-oxadiazolin-5-one (compound 54; XX, A=O, $R^1$=H, $R^2$=CH$_2$CH$_3$, $R^4$=C(CH$_3$)$_3$, X=F).

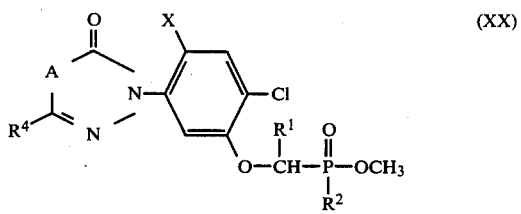

(XX)

EXAMPLE 18

A mixture of methyl P-methyl-1-(2,4-dichloro-5-hydrazinophenoxy)propylphosphinate (9.6 mmol) and pivaloylurea (9.6 mmol) in decahydronaphthalene (Decalin; 12 ml) is heated under reflux, with stirring, for about 8 hours, following the procedure of Gold-Aubert et al., Helvetia Chimica Acta 47(5):1188 (1964), to give, after purification, 3-t-butyl-1-{5-[α-(methyl P-methylphosphino)-n-propoxy]-2,4-dichlorophenyl}-$\Delta^2$-1,2,4-triazolin-5-one (compound 55; XX, A=NH, $R^1$=CH$_2$CH$_3$, $R^2$=CH$_3$, $R^4$=C(CH$_2$)$_3$, X=Cl).

In the same way, methyl P-ethyl-(2-chloro-4-fluoro-5-hydrazinophenoxy)methylphosphinate is reacted with formylurea to give 1-[5-methyl P-ethylphosphinomethoxy)-4-chloro-2-fluorophenyl]-$\Delta^2$-1,2,4-triazolin-5-one (compound 56; XX, A=NH, $R^1$=H, $R^2$=CH$_2$CH$_3$, $R^4$=H, X=F).

To the above triazolinone (2.5 mmol) is added methyl iodide (3.0 mmol), sodium hydride (2.5 mmol) and dimethylformamide (DMF; 15 ml). The mixture is heated at 80° for 3 hours. Upon cooling to RT, the reaction mixture is poured into water and extracted with methylene chloride. The combined extracts are washed with water, dried, evaporated to dryness and purified by prep. TLC to give 4-methyl-1-[5-(methyl P-ethylphosphinomethoxy)-4-chloro-2-fluorophenyl]-$\Delta^2$-1,2,4-triazolin-5-one (compound 57; XX, A=N(CH$_3$), $R^1$=H, $R^2$=CH$_2$CH$_3$, $R^4$=H, X=F).

EXAMPLE 19

To a solution of 2-chloro-4-fluoro-5-nitrophenol (100 mmol) in DMF (150 ml) is added Dabco (200 mmol) and dimethylthiocarbamoylchloride (150 mmol). The mixture is stirred at 50° for 5 hours, after which it is poured into water, taken up into ether and washed with dillute HCl and with brine. After the product has dried, solvent is removed and the residue is recrystallized to give O-(2-chloro-4-fluoro-5-nitrophenyl)dimethylthiocarbamate. This thiocarbamate is heated at 235° for about one hour to give S-(2-chloro-4-fluoro-5-nitrophenyl)dimethylthiocarbamate.

To a solution of S-(2-chloro-4-fluoro-5-nitrophenyl)dimethylthiocarbamate (4.20 g, 15.2 mmol) in ethanol (40 ml) and water (20 ml) is added ammonium chloride (0.81 g, 15.2 mmol) and iron (3.00 g, 53.0 mmol). The mixture is heated under reflux for two hours and is then filtered. The filtrate is concentrated to dryness, and the resulting residue is taken up in methylene chloride, washed, dried and evaporated to dryness to give S-(2-chloro-4-fluoro-5-aminophenyl)dimethylthiocarbamate.

The above aminophenylthiocarbamate (3.00 g) is treated with 5% aqueous NaOH (20 ml) in ethanol (20 ml) at reflux temperature overnight. The solvent is removed by evaporation, and the residue is diluted with water. The aqueous solution is neutralized with dilute HCl and the resulting precipitate is collected by filtration and dried to give 2-chloro-4-fluoro-5-aminophenylthiol.

Following the procedure of Example 10, 2-chloro-4-fluoro-5-aminophenylthiol is reacted with ethyl P-ethyl(methylsulfonyloxymethyl)phosphinate to give ethyl P-ethyl(2-chloro-4-fluoro-5-aminophenylthio)methylphosphinate, which is then reacted with 3,4,5,6-tetrahydrophthalic anhydride to yield N-[5-(ethyl P-ethylphosphinomethylthio)-4-chloro-2-fluorophenyl]tetrahydrophthalimide.

EXAMPLE 20

A mixture of methyl P-ethyl-[α-(2-chloro-5-aminophenoxy)-n-propyl]phosphinate (0.92 g, 3.2 mmol) and 3,4,5,6-tetrahydrophthalic anhydride (0.58 g, 3.8 mmol) in 5 ml of acetic acid is heated at 125° under N$_2$ for 20 hours. Acetic acid is removed in vacuo. The yellow oily product is purified by prep. TLC to give N-{5-[α-(methyl P-ethylphosphino)-n-propoxy]-4-chlorophenyl}tetrahydrophthalimide (compound 35, Table A).

nmr (CDCl$_3$) τ 8.78 (m, 6H, P—CH$_2$—CH$_3$, O—CH(CH$_2$CH$_3$)—P), 8.07 (m, 8H, CH$_2$—CH$_2$, P—CH$_2$—CH$_3$, O—CH(CH$_2$CH$_3$)—P), 6.32, 6.12 (dd, 3H, P—OCH$_3$), 5.42 (m, 1H, —CH(CH$_2$CH$_3$)—P), 2.87 (m, 3H, aromatic H).

In the same manner as above, ethyl P-ethyl[α-(2-chloro-5-aminophenoxy)-n-propyl]phosphinate (0.90 g, 3.1 mmol) and 3,4,5,6-tetrahydrophthalic anhydride (0.56 g, 3.7 mmol) are reacted together to give N-{5-[α-(ethyl P-ethylphosphino)-n-propoxy]-4-chlorophenyl} tetrahydrophthalimide (compound 36, Table A).

nmr (CDCl$_3$) τ 8.77 (m, 9H, O—CH$_2$—CH$_3$, P—CH$_2$—CH$_3$, O—CH(CH$_2$CH$_3$)—P), 8.20 (m, 8H, CH$_2$—CH$_2$, P—CH$_3$, O—CH(CH$_2$CH$_3$)—P), 5.70 (m, 3H, O—CH(CH$_2$CH$_3$)—P, O—CH$_2$—CH$_3$), 2.87 (m, 3H, aromatic H).

Each of methyl P-ethyl-[α-(2-chloro-5-aminophenoxy)-n-propyl]phosphinate and ethyl P-ethyl-[α-(2-chloro-5-aminophenoxy)-n-propyl]phosphinate is prepared following the procedure of Example 10 by reacting 2-chloro-5-aminophenol with, respectively, methyl P-ethyl-(α-methylsulfonyloxy-n-propyl)phosphinate and ethyl P-ethyl-(α-methylsulfonyloxy-n-propyl)phosphinate.

EXAMPLE 21

Following the procedure of Example 20, each of the phosphinates under column III is reacted with 2-chloro-5-aminophenol, followed by reaction with 3,4,5,6-tetrahydrophthalic anhydride to give the corresponding tetrahydrophthalimide in Table A.

III 43. ethyl P-methyl(α-methylsulfonyloxy-n-propyl)phosphinate
44. ethyl P-ethyl(methylsulfonyloxymethyl)phosphinate
45. ethyl P-isopropyl(α-methylsulfonyloxyethyl)phosphinate
46. ethyl P-ethyl(α-methylsulfonyloxyethyl)phosphinate
47. methyl P-ethyl(α-methylsulfonyloxyethyl)phosphinate
48. methyl P-ethyl(methylsulfonyloxymethyl)phosphinate

EXAMPLE 22

Following the procedure of Example 8, compounds 23, 25 and 30 are tested for pre-emergent herbicidal activity at 10 lb/acre and at 3.3 lb/acre. The average activity of the three compounds is presented in Table B below.

Following the procedure of Example 9, compounds 23, 25 and 30 are tested for postemergent herbicidal activity, at 10 lb/acre for grasses and at 10 lb/acre and 3.3 lb/acre for broadleafs. The average activity is presented in Table B below.

TABLE B

| | | % Average Herbicidal Activity | | | |
|---|---|---|---|---|---|
| | | Pre | | Post | |
| Cpd | lb/acre | GR | BL | GR | BL |
| 1 | 10 | 77 | 100 | 67 | 100 |
| | 3.3 | 63 | 93 | 73 | 100 |
| 3 | 10 | 82 | 100 | 100 | 90 |
| | 3.3 | 89 | 100 | 88 | 100 |
| 23 | 10 | 92 | 100 | 100 | 100 |
| | 3.3 | 90 | 100 | — | 100 |
| 25 | 10 | 100 | 100 | 100 | 100 |
| | 3.3 | 84 | 100 | — | 100 |
| 30 | 10 | 93 | 100 | 87 | 100 |
| | 3.3 | 76 | 100 | — | 100 |

What is claimed is:

1. A compound of the following formula (A):

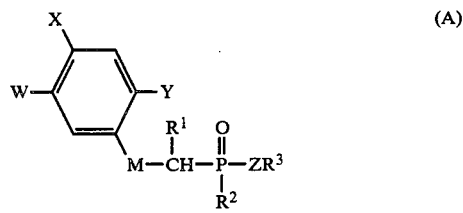

wherein,
M is oxygen, sulfur, sulfinyl or sulfonyl;
W is selected from the groups

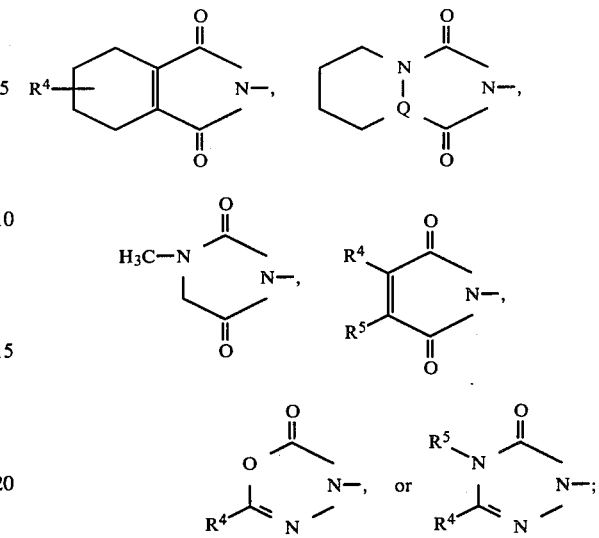

Q is N or CH;
each of X and Y is independently hydrogen or halogen;
Z is O, S or NR';
each of R' and $R^1$ is hydrogen or lower alkyl;
$R^2$ is lower alkyl or lower alkoxy;
$R^3$ is hydrogen, lower alkyl, lower alkenyl, lower alkynyl, cycloalkyl, alkoxyalkyl, alkylthioalkyl, alkoxycarbonylalkyl or dialkylaminocarbonylalkyl; and
each of $R^4$ and $R^5$ is independently hydrogen or lower alkyl.

2. A compound of the following formula, according to claim 1:

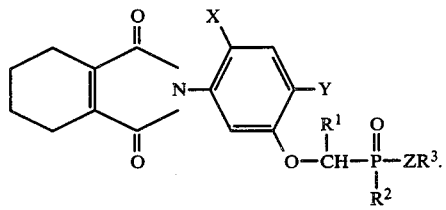

3. A compound according to claim 2 wherein $R^1$ is hydrogen, methyl or ethyl and $R^2$ is lower alkyl.

4. A compound according to claim 3 wherein $R^2$ is methyl, ethyl or n-propyl; $R^3$ is lower alkyl, alkoxyalkyl or alkoxycarbonylalkyl; and Z is oxygen.

5. A compound according to claim 4 wherein $R^3$ is methyl, ethyl, isopropyl, isobutyl or methoxyethyl.

6. A compound according to claim 5 wherein X is hydrogen, chloro or fluoro and Y is chloro.

7. The compound N-{5-[α-(methyl P-methylphosphino)ethoxy]-2,4-dichlorophenyl}tetrahydrophthalimide, according to claim 6.

8. The compound N-[5-(ethyl P-ethylphosphinomethoxy)-4-chloro-2-fluorophenyl]tetrahydrophthalimide, according to claim 6.

9. The compound N-{5-[α-(ethyl P-methylphosphino)-n-propoxy]-4-chloro-2-fluorophenyl}tetrahydrophthalimide, according to claim 6.

10. The compound N-{5-[α-(ethyl P-n-propylphosphino)ethoxy]-4-chloro-2-fluorophenyl}tetrahydrophthalimide, according to claim 6.

11. The compound N-[5-(isopropyl P-ethylphosphinomethoxy)-4-chloro-2-fluorophenyl]tetrahydrophthalimide, according to claim 6.

12. The compound N-[5-(isobutyl P-ethylphosphinomethoxy)-4-chloro-2-fluorophenyl]tetrahydrophthalimide, according to claim 6.

13. The compound N-[5-(methoxyethyl P-ethylphosphinomethoxy)-4-chloro-2-fluorophenyl]tetrahydrophthalimide, according to claim 6.

14. The compound N-{5-[α-(ethyl P-ethylphosphino)-n-propoxy]-4-chlorophenyl}tetrahydrophthalimide, according to claim 6.

15. The compound N-{5-[α-(methyl P-ethylphosphino)-n-propoxy]-4-chlorophenyl}tetrahydrophthalimide, according to claim 6.

16. A compound of the following formula, according to claim 1:

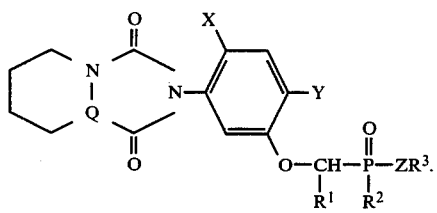

17. A compound according to claim 16 wherein Q is CH; Z is oxygen; $R^1$ is hydrogen, methyl or ethyl; X is hydrogen, chloro or fluoro; Y is chloro; and $R^2$ is lower alkyl.

18. A compound according to claim 17 wherein $R^3$ is lower alkyl, alkoxyalkyl or alkoxycarbonylalkyl.

19. A compound according to claim 18 wherein $R^2$ is methyl, ethyl or n-propyl and $R^3$ is methyl, ethyl, isopropyl or isobutyl.

20. The compound 3-{5-[α-(ethyl P-methylphosphino)-n-propoxy]-4-chloro-2-fluorophenyl}-1,5-tetramethylenehydantoin, according to claim 19.

21. A compound of the following formula, according to claim 1:

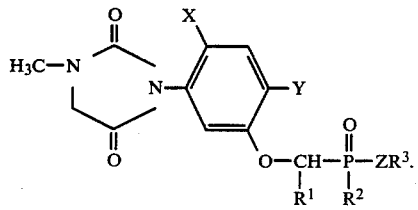

22. A compound according to claim 21 wherein $R^1$ is hydrogen, methyl or ethyl; $R^2$ is lower alkyl; $R^3$ is lower alkyl, alkoxyalkyl or alkoxycarbonylalkyl; X is hydrogen, chloro or fluoro; Y is chloro; and Z is oxygen.

23. A compound according to claim 22 wherein $R^2$ is methyl, ethyl or n-propyl and $R^3$ is methyl, ethyl, isopropyl or isobutyl.

24. A compound of the following formula, according to claim 1:

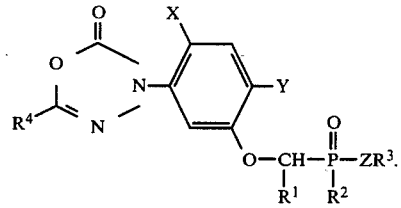

25. A compound according to claim 24 wherein $R^1$ is hydrogen, methyl or ethyl; $R^2$ is lower alkyl; $R^3$ is lower alkyl, alkoxyalkyl or alkoxycarbonylalkyl; $R^4$ is methyl, isopropyl or t-butyl; X is hydrogen, chloro or fluoro; Y is chloro; and Z is oxygen.

26. A compound according to claim 25 wherein $R^2$ is methyl, ethyl or n-propyl and $R^3$ is methyl, ethyl, isopropyl or isobutyl.

27. A compound selected from the following formula (III) or formula (IV):

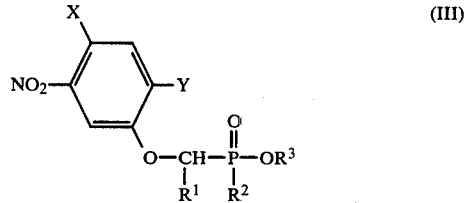

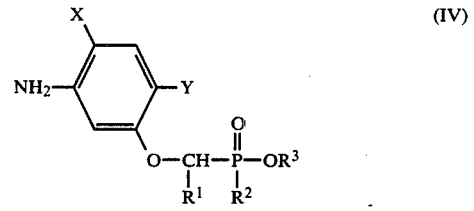

wherein, $R^1$ is hydrogen or lower alkyl;

$R^2$ is lower alkyl or lower alkoxy;

$R^3$ is hydrogen, lower alkyl, lower alkenyl, lower alkynyl, cycloalkyl, alkoxyalkyl, alkylthioalkyl, alkoxycarbonylalkyl or dialkylaminocarbonylalkyl; and each of X and Y is independently hydrogen or halogen.

* * * * *